United States Patent [19]

Dehoff et al.

[11] Patent Number: 5,718,585
[45] Date of Patent: Feb. 17, 1998

[54] PROSTHETIC TEETH AND MOLD MAKING THEREFOR

[75] Inventors: Barry Dehoff, York; Jeffrey McGraw, Boiling Springs; James McNulty; Vickie Reynolds, both of York; Roger Shue, Red Lion; Mark White, Shrewsbury, all of Pa.

[73] Assignee: Dentsply Research & Development Corp., Milford, Del.

[21] Appl. No.: 528,832

[22] Filed: Sep. 15, 1995

[51] Int. Cl.⁶ .................................................. A61C 13/08
[52] U.S. Cl. .................................. 433/202.1; 433/203.1
[58] Field of Search ........................... 433/202.1, 203.1, 433/218, 219, 223, 229

[56] References Cited

U.S. PATENT DOCUMENTS

| | | | |
|---|---|---|---|
| 3,861,044 | 1/1975 | Swinson, Jr. | 32/17 |
| 4,324,546 | 4/1982 | Heitlinger et al. | 433/25 |
| 4,411,626 | 10/1983 | Becker et al. | 433/223 |
| 4,436,684 | 3/1984 | White | 264/138 |
| 4,575,805 | 3/1986 | Moermann et al. | 364/474 |
| 4,611,288 | 9/1986 | Duret et al. | 364/474 |
| 4,615,678 | 10/1986 | Moermann et al. | 433/201.1 |
| 4,663,720 | 5/1987 | Duret et al. | 364/474 |
| 4,742,464 | 5/1988 | Duret et al. | 364/474 |
| 4,766,704 | 8/1988 | Brandestini et al. | 51/327 |
| 4,795,345 | 1/1989 | Ai et al. | 433/202.1 |
| 4,833,617 | 5/1989 | Wang | 364/474.15 |
| 4,837,732 | 6/1989 | Brandestini et al. | 364/413.28 |
| 4,909,738 | 3/1990 | Ai et al. | 433/202.1 |
| 4,969,817 | 11/1990 | Hiranuma et al. | 433/202.1 |
| 5,027,281 | 6/1991 | Renow et al. | 364/474.24 |
| 5,033,014 | 7/1991 | Carver et al. | 364/571.01 |
| 5,092,022 | 3/1992 | Duret | 29/160.6 |
| 5,151,044 | 9/1992 | Rotsaert | 433/202.1 X |
| 5,224,049 | 6/1993 | Mushabac | 364/474.05 |
| 5,452,219 | 9/1995 | Dehoff et al. | 364/474.05 |
| 5,624,262 | 4/1997 | Yarovesky et al. | 433/203.1 |

FOREIGN PATENT DOCUMENTS

| | | |
|---|---|---|
| 0 541 500 | 5/1993 | European Pat. Off. |
| 40 34 007 | 4/1992 | Germany |
| 2 197 502 | 5/1988 | United Kingdom |
| 91/13988 | 4/1991 | WIPO |
| 91/18356 | 11/1991 | WIPO |

*Primary Examiner*—Nicholas D. Lucchesi
*Attorney, Agent, or Firm*—Dale R. Lovercheck; James B. Bieber

[57] ABSTRACT

A prosthetic tooth having an enamel layer which has a zone of substantially constant thickness. This tooth is molded using a dental tooth mold part prepared by imaging a dental pattern of a prosthetic tooth shade layer and/or shader mold part outer surface, and forming the dental pattern in a mold by program directed milling. A family of prosthetic teeth is provided including a first tooth in a first set of teeth having a first overall labial length, and a first back length, and a second tooth in a second set of teeth having a second overall labial length, and a second back length. The invention provides a prosthetic incisor tooth including a tooth body having two generally symmetrical curved grooves between three curved ridges on the labial face of the body at the incisal end of the body. The grooves are deepest at the incisal end and extend substantially from the incisal edge to at least about 15 percent of the overall tooth length.

24 Claims, 10 Drawing Sheets

PROSTHETIC TEETH AND MOLD MAKING THEREFOR

The invention relates to prosthetic teeth and the fabrication of mold parts to make prosthetic teeth. The invention provides multiple part dental tooth molds and prosthetic teeth with an enamel layer having zones of uniform thickness. Prosthetic teeth in accordance with a preferred embodiment of the invention are readily articulable within sets and proportionally consistent within families. Prosthetic teeth in accordance with the invention are useful for making full and/or partial dentures, and as crowns, implant teeth and shade guides having prosthetic teeth thereon.

Tooth molds are used in the dental industry for the manufacture of artificial teeth. Refining steps include a final finish-polish step, which provides a mold of high-definition of the surface properties of the artificial tooth to be produced by molding tooth making material therein.

Dehoff et al in U.S. Pat. No. 5,452,219 (Case 1619) disclose a method for making a tooth mold. Erdle in Australia 124,083 disclose ceramic articles and material and method for coloring or shading the same. Saffir in U.S. Pat. No. 2,380,568 disclose artificial tooth. Kelly in U.S. Pat. No. 2,514,075 disclose artificial tooth. Erdle in U.S. Pat. No. 2,517,100 disclose method of forming ceramic articles and producing different colors or shades along different potions of the article. Budish in U.S. Pat. No. 2,643,455 disclose artificial teeth. Rydin in U.S. Pat. No. 2,677,150 disclose method in producing artificial teeth. Slack, Jr. in U.S. Pat. No. 2,678,470 disclose polymerizing method. Saffir in U.S. Pat. No. 3,126,429 disclose method of casting teeth having different colored layers. Connan in U.S. Pat. No. 3,218,711 disclose artificial teeth. Swinson in U.S. Pat. No. 3,861,044 teaches a method of fitting a tooth with a dental inlay. Heitlinger et al. in U.S. Pat. No. 4,324,546 disclose an apparatus and method for the manufacture of dentures. Tanaka in U.S. Pat. No. 4,392,829 disclose metal porcelain dental restoration and method of making. Faunce in U.S. Pat. No. 4,433,959 disclose composite laminate dental veneer containing color systems. White in U.S. Pat. No. 4,436,684 describes methods of making three dimension models and mold cavities of internal body structure.

Tanaka in U.S. Pat. No. 4,481,227 disclose method of coloring bakable porcelain dental restorations. Moermann et al. in U.S. Pat. No. 4,575,805 disclose a method and a apparatus for the fabrication of custom-shaped implants.

Duret et al. in U.S. Pat. No. 4,611,288 describe a system for taking an impression of a body region for the production of a prosthesis.

Moermann et al. in U.S. Pat. No. 4,615,678 teach a blank from which an implant can be machined by an apparatus of the type disclosed in U.S. Pat. No. 4,575,805. Miller in U.S. Pat. No. 4,617,159 disclose method of molding a dental shade sample. Amdur et al. in U.S. Pat. No. 4,645,454 disclose porcelain products and methods. Blair et al. in U.S. Pat. No. 4,650,418 disclose dental restoration shading. Duret et al. in U.S. Pat. Nos. 4,663,720 and 4,742,464 disclose a method of making a dental prosthesis. Watanabe et al. in U.S. Pat. No. 4,681,633 disclose high strength calcium phosphate glass ceramic materials. Corbett in U.S. Pat. No. 4,722,689 disclose coated temporary dental crowns. Brandestini et al. in U.S. Pat. No. 4,766,704 describe a method and apparatus for machining a custom-shaped dental restorative part from a blank of dental material in a single operation. Brandestini et al. in U.S. Pat. No. 4,837,732 teach a method of facilitating acquisition of data defining the three-dimensional shape of prepared teeth and their immediate vicinity.

Rotsaert in U.S. Pat. No. 4,970,032 disclose processes for the manufacture of artificial teeth and crowns. Grossman et al. in U.S. Pat. No. 5,089,306 disclose glazing dental constructs. Hasegawa et al. in U.S. Pat. No. 5,127,834 disclose artificial teeth and method for making them. Rotsaert in U.S. Pat. No. 5,151,044 disclose blanks for the manufacture of artificial teeth and crowns. Emmons in U.S. Pat. No. 5,308,243 disclose method and compositions for producing life-like dental porcelain restorations and dental porcelain restorations so produced. Oden in U.S. Pat. No. 5,342,201 disclose method of manufacturing ceramic artificial tooth restorations.

It is an object of the invention to provide artificial teeth with an enamel layer having zones of constant thickness.

It is an object of the invention to provide a family of prosthetic teeth, including a first tooth in a first set of teeth having a first overall labial length, and a first back length, and a second tooth in a second set of teeth having a second overall labial length, and a second back length, wherein the ratio of the first to the second overall labial length is substantially equal to the ratio of the first to the second back length.

It is an object of the invention to provide a prosthetic tooth including a tooth body having two generally symmetrical curved grooves between three curved ridges on the labial face of the body at the incisal end of the body, wherein the grooves are deepest at the incisal end and extend substantially from the incisal edge to at least about 15 percent of the overall tooth length.

It is an object of the invention to provide an image of at least a portion of at least one upper tooth and at least one lower tooth, each said tooth being from the same side of the same set of teeth, modifying initial data corresponding to the image to form modified data, molding modified prosthetic teeth in molds made using the modified data, whereby, during articulation the modified prosthetic teeth contact along a larger proportion of tooth surface than prosthetic teeth made in molds using the initial data.

Set of teeth as used herein refers to teeth to be used for the same individual, such as is a single denture whether full or partial.

Family of teeth as used herein refers to sets of teeth of different sizes and/or shades but having common shapes.

SUMMARY OF THE INVENTION

A prosthetic tooth having an enamel layer which has a zone of substantially constant thickness. This tooth is molded using a dental tooth mold part prepared by imaging a dental pattern of a prosthetic tooth shade layer and/or shader mold part outer surface, and forming the dental pattern in a mold by program directed milling.

The invention provides a family of prosthetic teeth, including a first tooth in a first set of teeth has a first overall labial length, and a first back length, and a second tooth in a second set of teeth has a second overall labial length, and a second back length. The ratio of the first overall labial length to the second overall labial length is substantially equal to the ratio of the first back length to the second back length. Preferably the first tooth has a first shade length and the second tooth has a second shade length and the ratio of the first shade length to the first overall labial length is substantially equal to the ratio of the second shade length to the second overall labial length.

The invention provides a prosthetic tooth including a tooth body having two generally symmetrical curved grooves between three curved ridges on the labial face of the body at the incisal end of the body. The grooves are deepest at the incisal end and extend substantially from the incisal edge to at least about 15 percent of the overall tooth length.

The invention provides a method of making readily articulable prosthetic teeth by displaying an image of at least a portion of at least one upper tooth and at least one lower tooth from the same side of the same set of teeth, then modifying initial data corresponding to the image to form modified data, molding readily articulable prosthetic teeth in molds made using the modified data, whereby, during articulation the readily articulable prosthetic teeth contact along a larger proportion of tooth surface than prosthetic teeth made in molds using the initial data.

DESCRIPTION OF THE PREFERRED EMBODIMENTS

Figure 1:
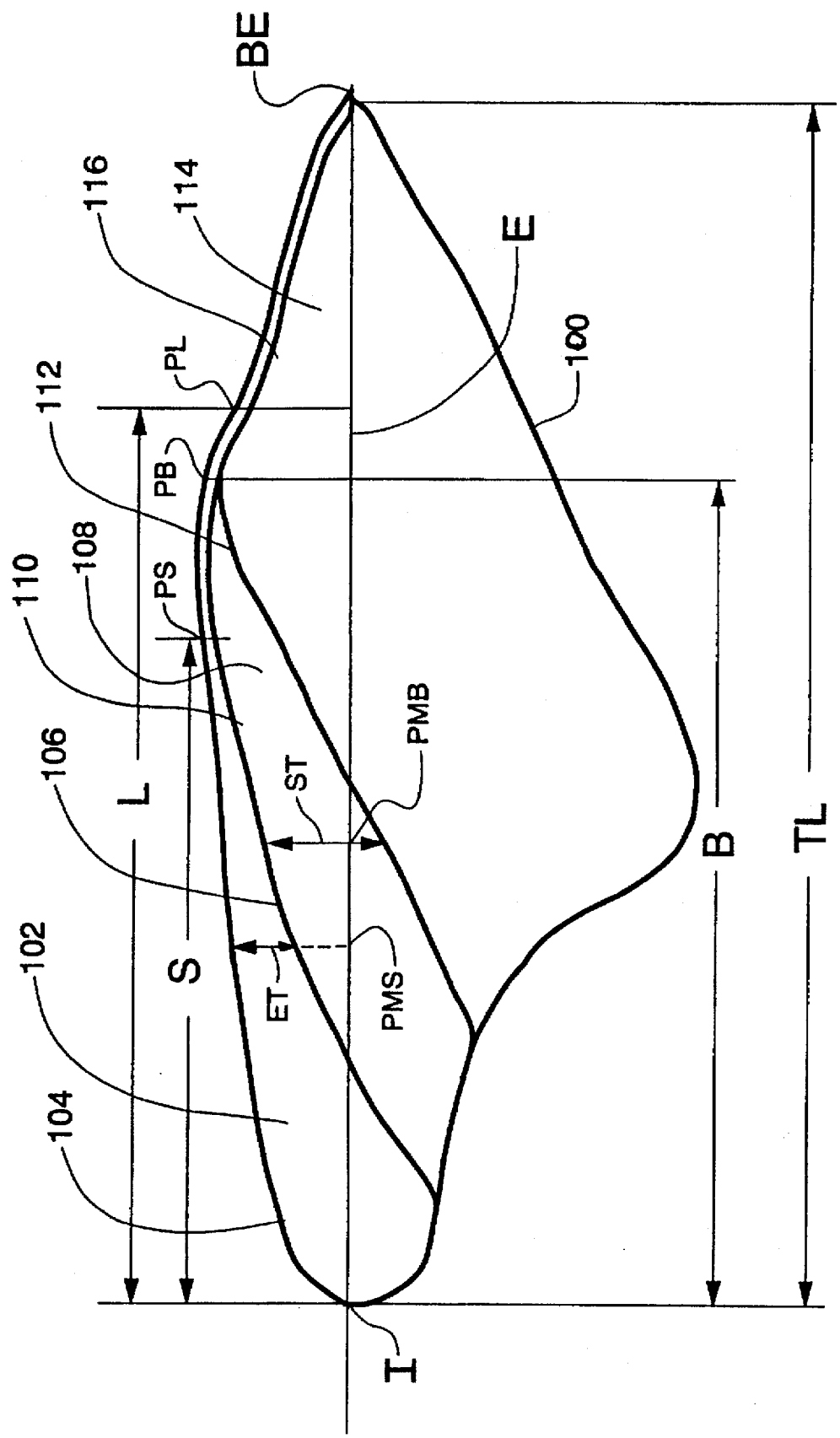
FIG. 1 is a schematic side view of a prosthetic tooth in accordance with the invention.

The invention is now described with more particular references to FIGS. 1–8. A prosthetic tooth 100 in accordance with a preferred embodiment of the invention includes enamel layer 102 having labial face 104 and shader face 106, shade layer 108 having enamel face 110 and back face 112 and back layer 114 having shader face 116 as shown in FIG. 1. The overall tooth length (TL) as used herein refers to the distance measured along the elongated central axis (E) of the tooth from the tip of the incisal edge (I) of a tooth to the point (BE) on the edge of back 114 furthest from the incisal edge (I).

Overall labial length (L) as used herein refers to the distance measured along the elongated central axis (E) of the tooth from the tip of the incisal edge (I) of a tooth to the point (PL) on the outer face of the neck of the tooth midway between the highest and the lowest points on the neck as shown in FIG. 1.

Back length (B) as used herein refers to the distance measured along the elongated central axis (E) of the tooth from the tip of the incisal edge (I) of a tooth to the end of the second back layer (PB) which is preferably about the highest point on the neck as shown in FIG. 1. The shade layer thickness (ST) at the midpoint (PMB) of the back length (B) is preferably about 0.09 inch.

Shade layer length (S) as used herein refers to the distance measured along the elongated central axis (E) of the tooth from the tip of the incisal edge (I) of a tooth to the point (PS) wherein the enamel layer changes from decreasing to constant thickness as shown in FIG. 1. The enamel thickness (ET) at the midpoint (PMS) of the shade layer length(s) is preferably about 0.031 inch.

Multiple layered teeth are provided that have a uniform thickness of enamel across a latitudinal cross section from the neck of the tooth to the center of the labial surface. This uniform enamel thickness is imaged by offsetting a copy of the labial surface of an anterior tooth and partially shaping the offset copy of the enamel surface into a curved surface to form an image of a shade layer outer surface. A shader mold part is later cut into a solid block of material, preferably metal, to provide a mold surface corresponding to the image of the shade layer outer surface.

Figure 1A:
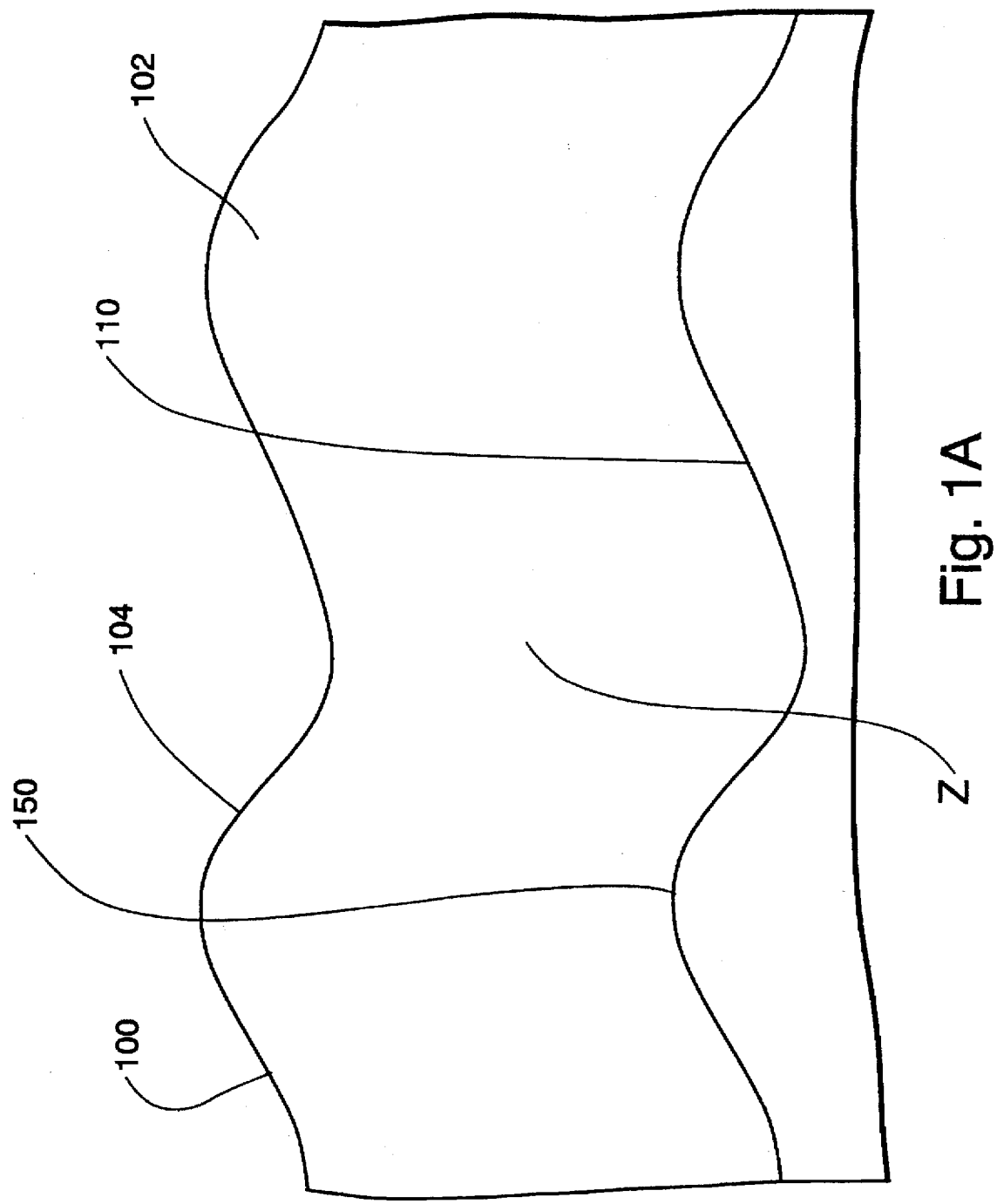
FIG. 1A is a partial schematic side view of a prosthetic tooth in accordance with the invention.

As shown in FIGS. 1 and 1A prosthetic tooth 100 includes an enamel layer 102 having a zone Z of substantially constant enamel thickness. The enamel thickness extending normal to the central axis E of the tooth at any point, for example point 150, selected on the labial face 104 is within 0.003 inch of the thickness at any other point within 0.005 inch of the selected point. In a preferred embodiment of the invention the enamel thickness has an average thickness and said average thickness varies less than 20 percent within said zone, and said zone is circular having a diameter of at least 0.01 inch. The zone of substantially constant thickness extends preferably at least between 20 percent and 75 percent of the overall labial length of the tooth. Preferably the substantially constant enamel thickness varies less than 25 percent within any enamel zone which extends normal to the shade layer, and the zone is at least 2 mm$^2$ more preferably at least 4 mm$^2$ and most preferably at least 8 mm$^2$. More preferably the substantially constant enamel thickness varies less than 20 percent within the zone. Preferably the area of the zone is substantially circular. Preferably the enamel thickness is between about 0.003 and about 0.03 inches. Preferably the enamel thickness is between about 0.08 and 0.03 inches toward the incisal end of the tooth. Preferably the enamel thickness is less than 0.003 inches toward the back end of the tooth. Preferably the tooth has a neck member. Preferably the tooth includes two overall symmetrical regions between three substantially thicker regions on the labial face of the body at the incisal end of the body between 0 and 20 percent of the overall tooth length.

Figure 6:
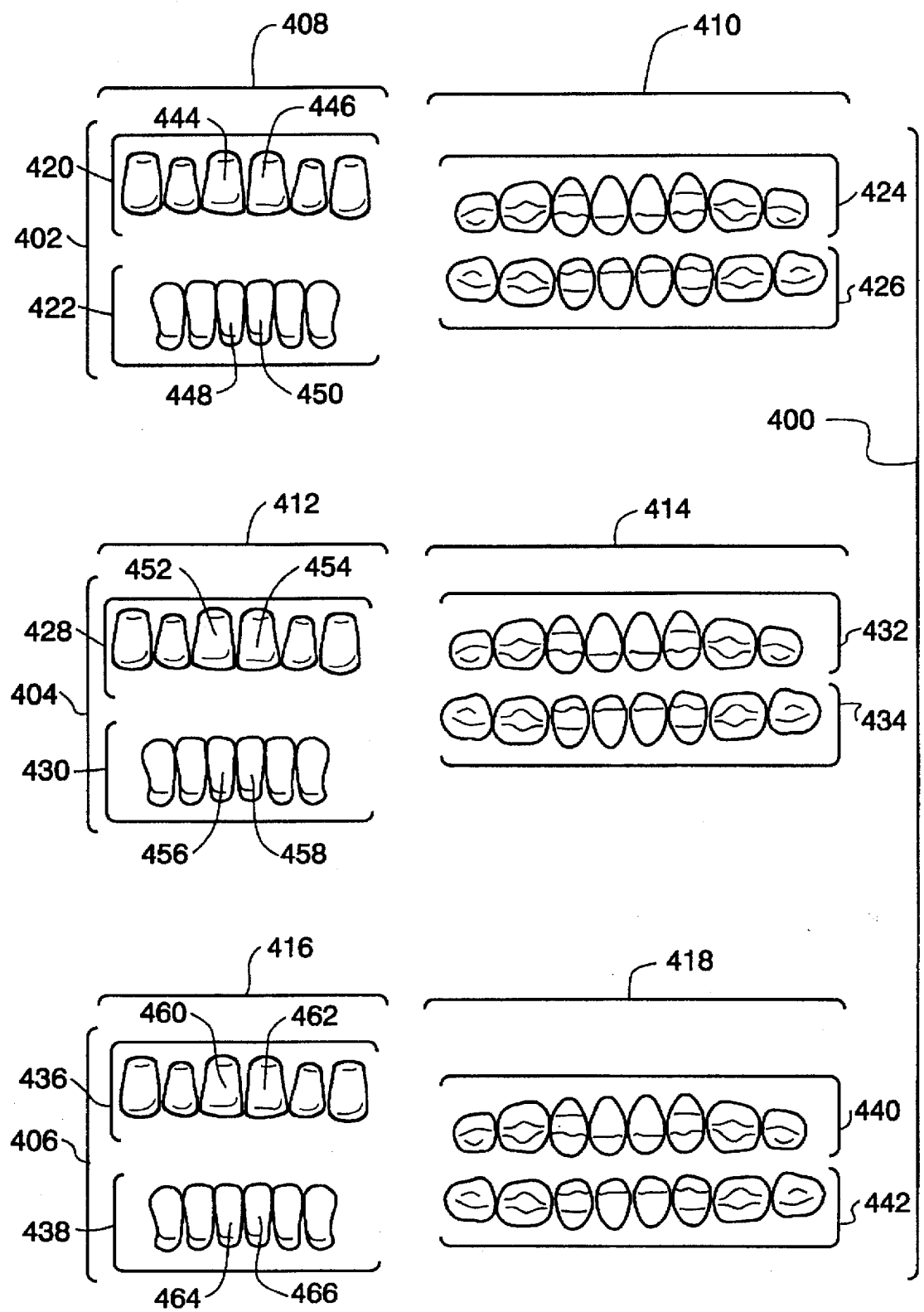
FIG. 6 is a schematic view of a family of prosthetic tooth sets in accordance with the invention.

Preferably within a family of teeth multi-layered anterior teeth are provided that have constant dimensional ratios. These dimensions are measured on longitudinal cross sections of the teeth from the family of teeth as shown in FIGS. 1 and 6.

Posterior teeth are provided in accordance with the invention that have constant dimensional ratios. All teeth within a family of such teeth exhibit similar characteristics for making a denture. Articulation of upper and lower teeth made in accordance with the invention is easier and more complete than it is for prior art teeth. Small, medium and large teeth within a family all exhibit the same articulation characteristics.

Three-dimensional tooth surface, tooth layer, and/or tooth mold part patterns are displayed on video display monitors from stored, edited and/or digitized data. The operator examines, measures and/or modifies qualities of the surface pattern such as the size and shape of the tooth and labial striations, desired for the dental mold. By visual analysis and comparison to known geometric values, e.g., length, width, thickness, for the teeth, the operator determines to add, and/or omit data via input devices, such as a keyboard. A desired three-dimensional surface pattern is thus created and displayed.

The data used for the three-dimensional surface pattern displayed is used by CAM or computer-assisted manufacture to produce a tool path program for the fabrication of the dental mold. The tool path program is used to direct and control a machine tool. The machine is preferably of multi-axes. The program will direct a milling cutter or cutters in the milling of a tooth mold from a suitable substrate, for example, steel, nickel, aluminum, ceramic, plastic or any machinable material. Steel is the preferred substrate. After the mold has been cut, the tool path program is preferably used to direct and control the application of the finish-polish to the mold. The finish-polish step improves the surface finish and results in a mold suitable for the manufacture of artificial teeth. A final hand-applied finish-polish step is optional.

Tooth molds for the manufacture of an artificial tooth requires a high degree of definition to produce the labial striations or markings on a tooth and multiple molds are needed to produce a blend of color capable of producing a natural appearance in the artificial tooth.

Imaging of enamel, shader, and back and second back mold parts is useful in accordance with a preferred embodiment of the invention to make mold parts for production of central, lateral, and canine prosthetic teeth. Size proportioning for imaged enamel, shader back and second back for different sets of teeth with a family of teeth provides proportional consistency of the teeth within the family. Specific points are selected and distances there between are maintained proportionally constant within a family of teeth. Preferably thickness dimensions are measured from the facial topography to keep consistency in the shape of the tooth and in the enamel thickness.

In accordance with a preferred embodiment of the invention a shader and second back are imaged by first determining the overall labial length (L) of the tooth. The location of the shader and second back blend starting locations PS and PB respectively are determined by multiplying the overall labial length (L) of the tooth by a different constant for each tooth set of a tooth family. The back length (B) is then broken into portions each represented by a constant for each tooth set within a tooth family. The shape and location of shader mold surface contours for central and lateral teeth and/or blend thicknesses are determined and/or developed.

Figure 2:
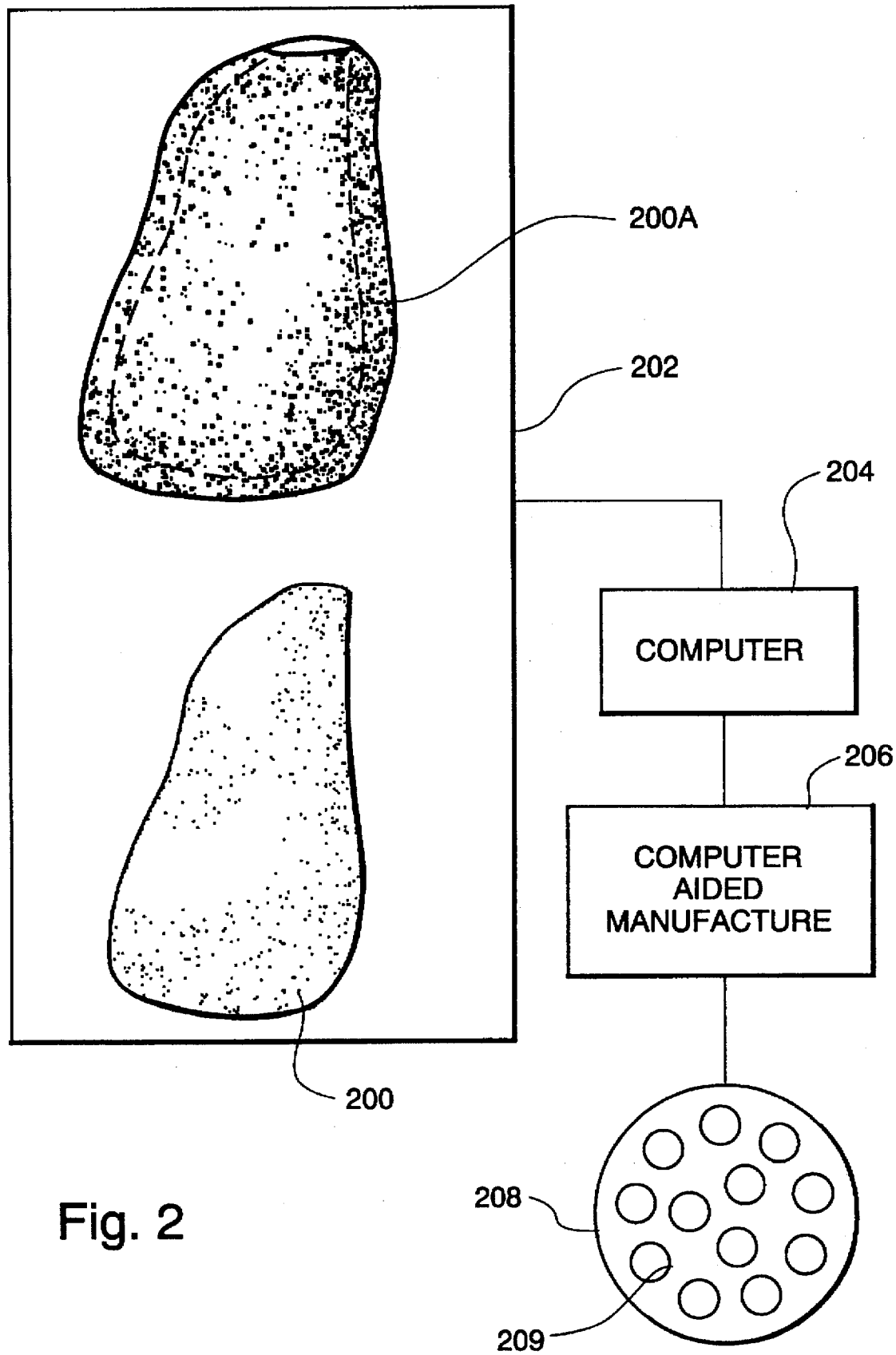
FIG. 2 is a schematic perspective view of a system displaying an enamel layer and an enamel mold part in accordance with the present invention.
Figure 3:
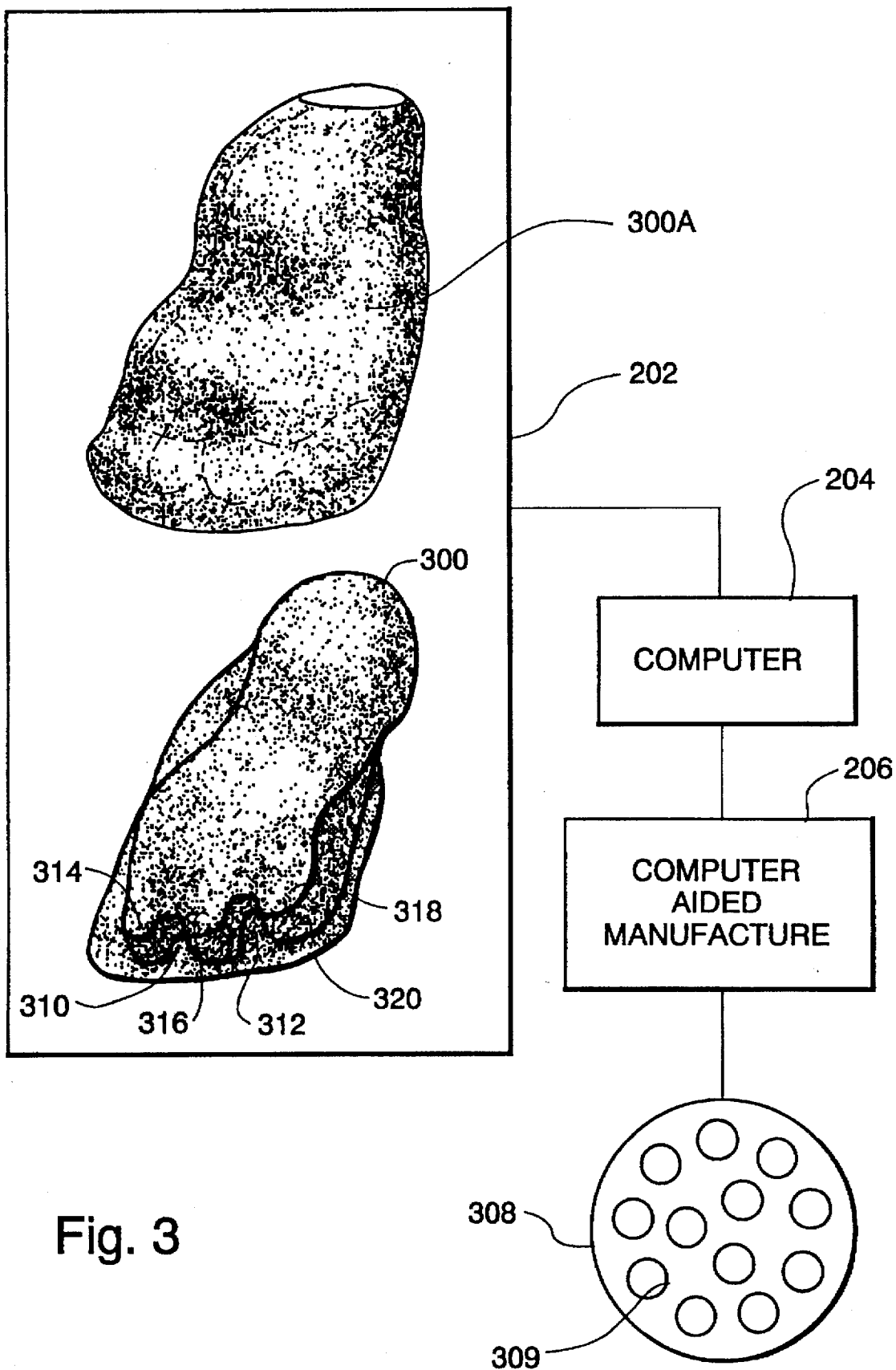
FIG. 3 is a schematic perspective view of a system displaying a shade layer and a shader mold part in accordance with the invention.
Figure 4:
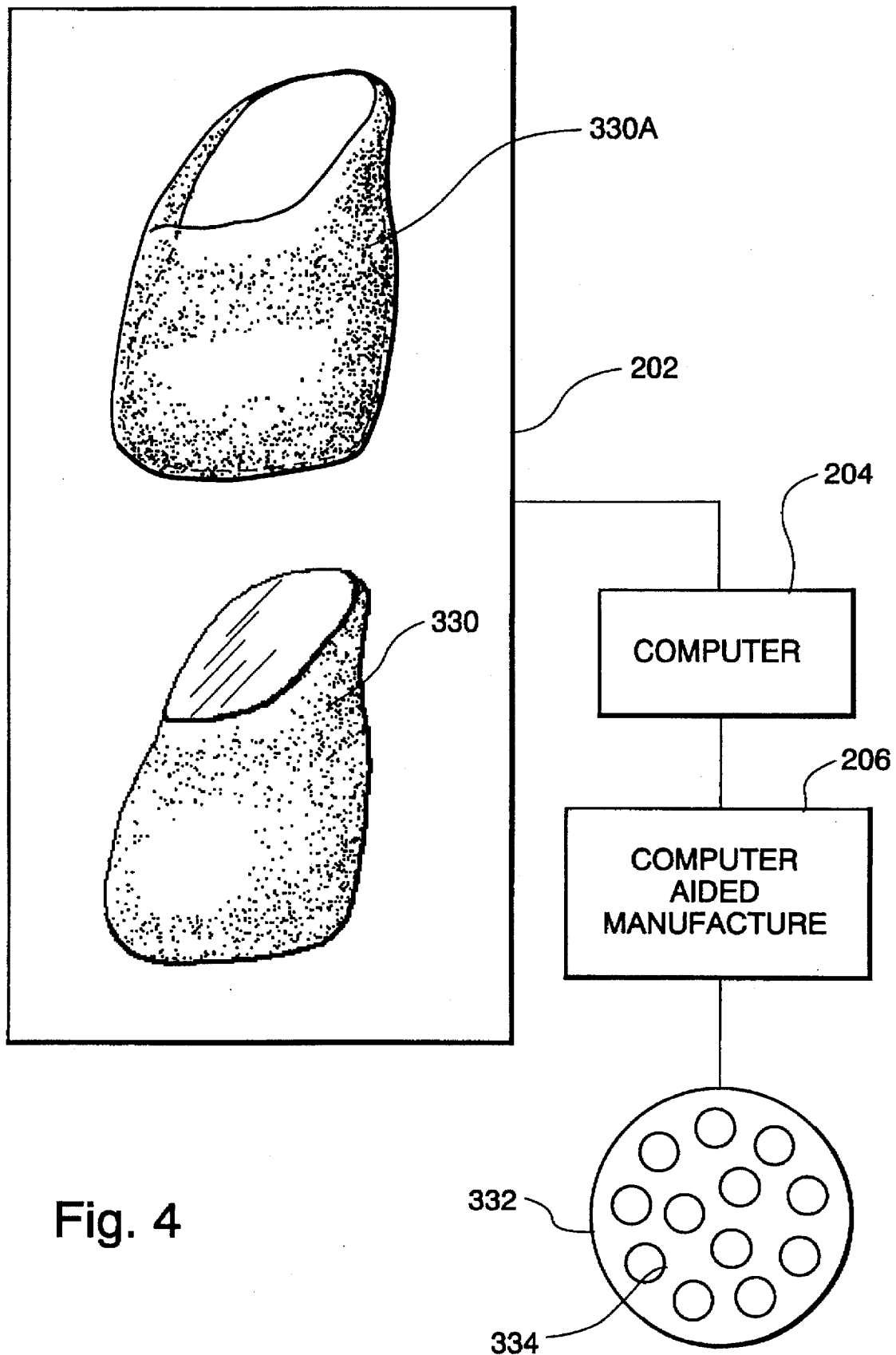
FIG. 4 is a schematic perspective view of a system displaying a second back layer and a second back mold part in accordance with the invention.
Figure 5:
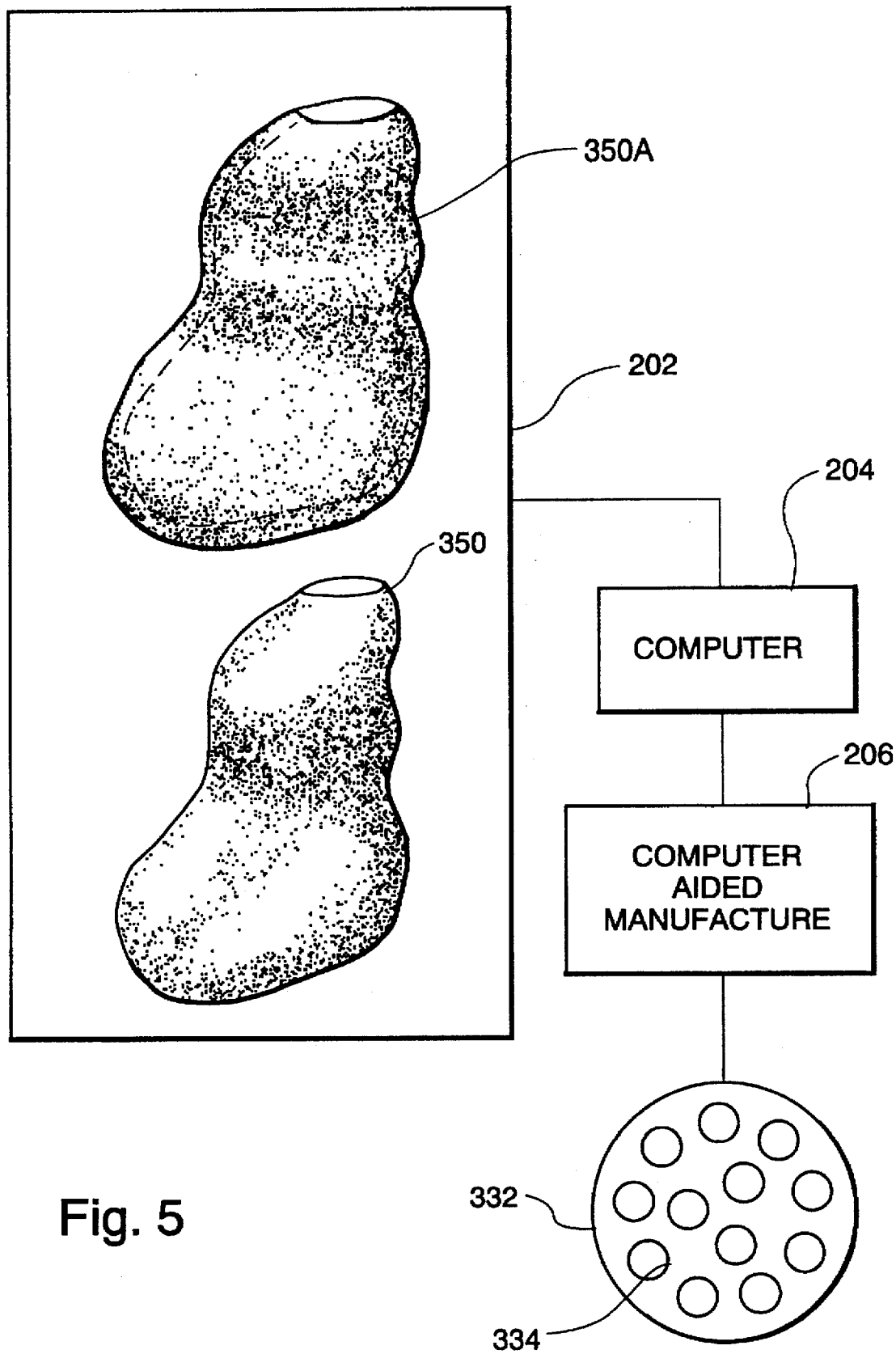
FIG. 5 is a schematic perspective view of a of a system displaying a back layer and a back mold part in accordance with the invention.

Images of an enamel mold part 200 and enamel layer 200A on display 202 are shown in FIG. 2. Images of shader mold part 300 and shade layer 300A are shown in FIG. 3 images of second back mold part 330 and second back layer 330A are shown in FIG. 4. Images of back mold part 350 and back layer 350A are shown in FIG. 5. Display 202 is connected to computer system 204. Preferably a tooth enamel mold part 208 is milled in a metal substrate by computer aided manufacture system 206. Mold parts 208, 308, 332 and 352 are cut by computer aided manufacture system 206 with multiple molding sites 209, 309, 334 and 354 as shown in FIGS. 2 through 5. Preferably a prosthetic dental tooth, such as tooth 100, having a shade layer, such as shade layer 108, corresponding to shade layer image 300 is formed in a molding site of a shader mold part, such as shader mold part 308. Each mold part is cut by computer aided manufacture system 206 with multiple molding sites therein, each of which is adapted to form a layer of a tooth corresponding to a layer image. Preferably the forming includes using a tool path program to direct machine cutting and/or finishing-polishing the tooth mold part. Preferably polymerizable acrylate material is sequentially inserted between pairs of mold parts to sequentially form a prosthetic tooth having enamel, shade, second back, and back layers. Thus, a preferred embodiment of the invention provides a prosthetic tooth including an enamel layer, a shade layer, a second back layer and a back layer as shown in FIG. 1.

Shade layer 300 has two generally symmetrical curved grooves corresponding to groove images 310 and 312 between three curved ridges corresponding to ridge images 314, 316 and 318, on the labial face of the shade layer at the incisal end of the tooth, as shown in FIG. 3. The grooves are deepest at the incisal end and extend substantially from the incisal edge to at least about 15 percent of the overall tooth length. Each groove 310 and 312 has a bottom that is substantially smooth. The sides of grooves 310 and 312 intersect the plane of the top of ridges 31, 316 and 318 at the ends of the grooves opposite to the incisal end 320. Grooves 310 and 312 extend at least about 5 percent of the lengths of shade layer 300. Preferably the tooth includes a tooth shade layer and a tooth enamel layer. Preferably the depth of each groove is from about 0.5 to 1.5 times the width of each groove. Preferably the cross section of the shader mold upper surface adjacent to the incisal edge forms a sine curve.

Figure 5A:
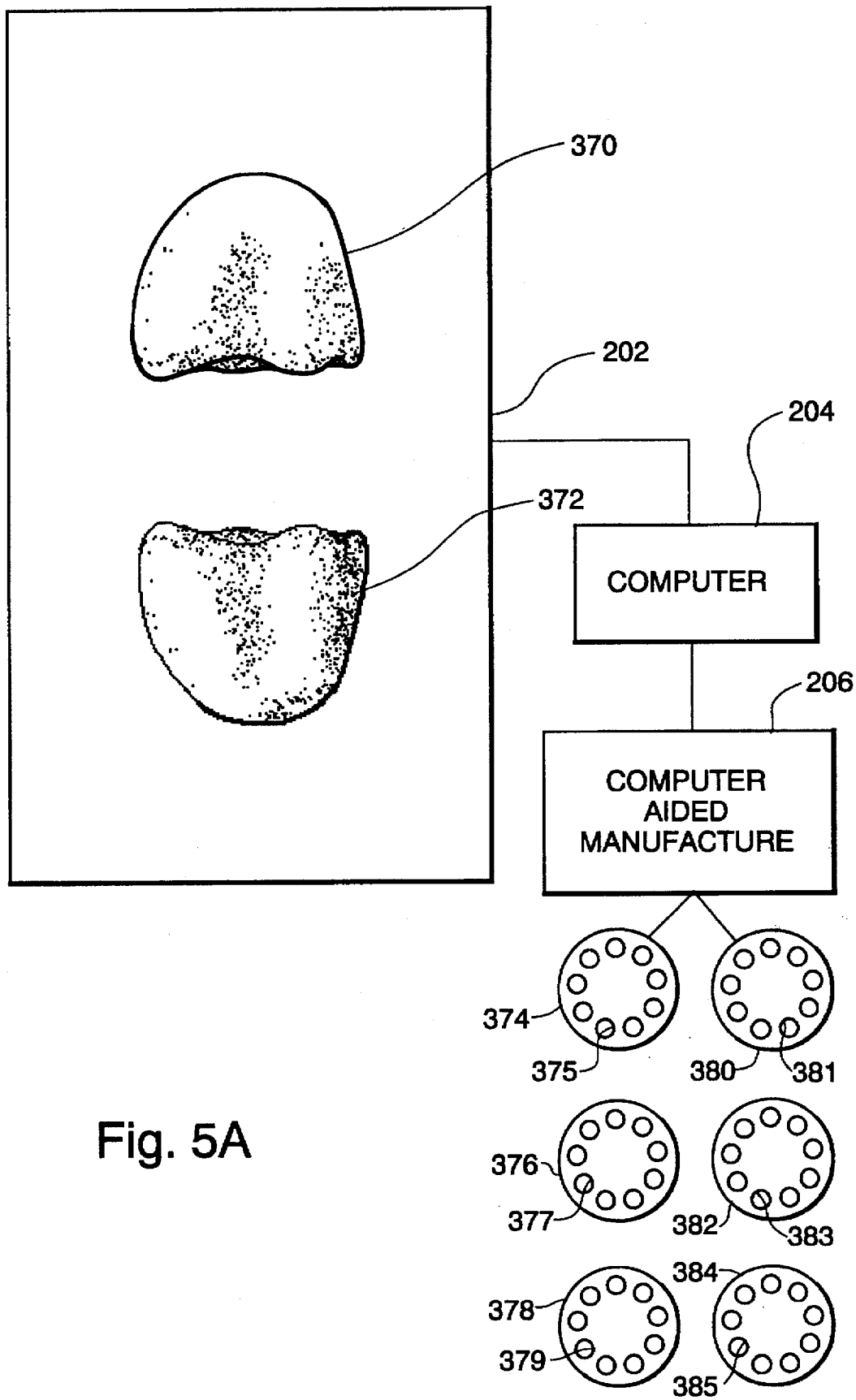
FIG. 5A is a schematic perspective view of a system displaying upper and lower molar teeth in accordance with the invention.

As shown in FIG. 5A molds for making readily articulable prosthetic teeth, are made by displaying an image of at least a portion of at least one upper tooth and at least one lower tooth. Each tooth is from the same side of the same set of teeth. Data corresponding to the image is modified whereby at least a portion of at least one is more nearly parallel to at least a portion of the other tooth image. Teeth are molded in molds made using the data. During articulation of these molded prosthetic teeth the upper and the lower molded prosthetic tooth contact along a larger proportion of each tooth surface than would be contacted without previously modifying while displaying the image of the tooth.

In accordance with a preferred embodiment of the invention is provided a method of forming a shade pattern in a tooth including imaging an outer surface for a shader mold part from a labial surface image for a face mold part, cutting a shader mold part using a tool path program, and molding a tooth having a shade pattern in a mold having the shader mold part.

In accordance with a preferred embodiment of the invention is provided a tooth family including a first tooth in a first family and a second tooth in a second family. The first tooth has a first ratio of the overall tooth length to the distance from the deepest point on the labial surface of the neck of the tooth to the incisal edge of the tooth. The second tooth has a second ratio of the overall tooth length to the distance from the deepest point on the labial surface of the neck of the tooth to the incisal edge of the tooth. The first and second ratio being substantially equal. Such prosthetic teeth are preferably provided in a set which includes a first tooth having a first outer surface and a second tooth having a second outer surface.

In a preferred embodiment of the invention as shown in FIG. 6 is provided a family of prosthetic teeth 400. Family of teeth 400 includes sets of teeth 402, 404 and 406. Set of teeth 406 includes anterior teeth 408 and posterior teeth 410. Set of teeth 404 includes anterior teeth 412 and posterior teeth 414. Set of teeth 406 includes anterior teeth 416 and posterior teeth 418. Anterior teeth 408 include upper teeth 420 and lower teeth 422. Posterior teeth 410 include upper teeth 424 and lower teeth 426. Anterior teeth 412 include upper teeth 428 and lower teeth 430. Posterior teeth 414 include upper teeth 432 and lower teeth 434. Anterior teeth 416 include upper teeth 436 and lower teeth 438. Posterior teeth 418 include upper teeth 440 and lower teeth 442. Upper anterior central teeth 444 and 446, have shapes which are mirror images of each other. Upper anterior teeth 428 include central teeth 452 and 454 which have shapes which are mirror images of each other. Lower central teeth 448 and 450 have shapes which are mirror images of each other. Lower central teeth 456 and 458 have shapes which are mirror images of each other. Lower central teeth 464 and 466 have shapes which are mirror images of each other.

Tooth 444 in set of teeth 402 has a first overall labial length, and a first back length. Tooth 452 in set of teeth 404 has a second overall labial length, and a second back length. The ratio of the first overall labial length to the second overall labial length is substantially equal to the ratio of the first back length to the second back length. Tooth 404 has a first shader length and tooth 452 has a second shader length and the ratio of the first shader length to the first overall labial length is substantially equal to the ratio of the second shader length to the second overall labial length. Preferably this consistency of these ratio is present in corresponding molar, incisor and canine teeth of different sets within family 400. Preferably the back length is substantially equal to 94 percent of the overall labial length. Preferably the shader length is substantially equal to 68 percent of the overall labial length.

Preferably the enamel thickness of prosthetic teeth of the invention varies less than 20 percent within a circular zone having a diameter equal to the thickness. More preferably the enamel thickness varies less than 15 percent within a circular zone having a diameter equal to twice the thickness of the enamel. Most preferably the enamel thickness varies less than 25 percent within a circular zone having a diameter equal to thrice the thickness.

Preferably the enamel thickness at a selected point on the labial face between 20 percent and 75 percent of the overall labial length of the tooth is within 0.003 inch of the thickness at any other point within 0.005 inch of the selected point. Preferably the outer surface of the enamel and the interface of the enamel with the shade layer having substantially the same contours within a zone of constant enamel thickness.

Figure 7:
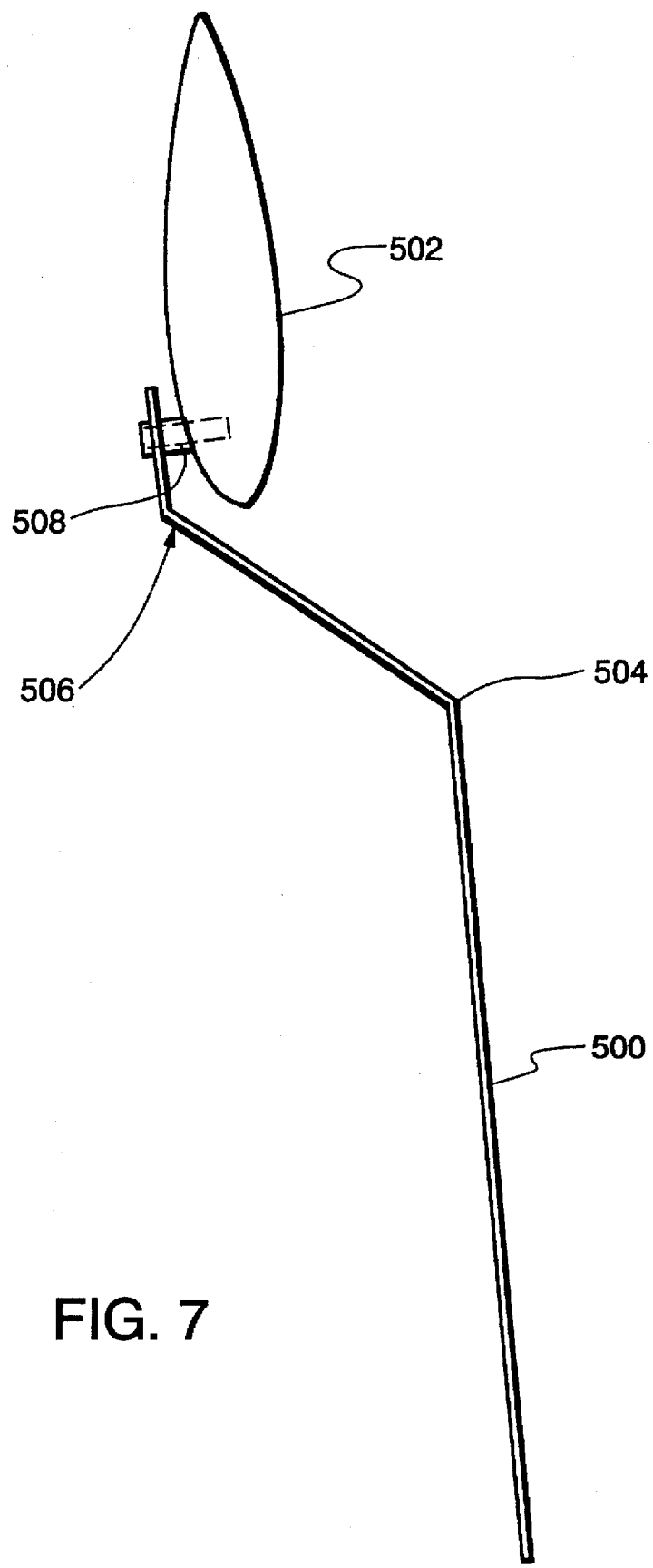
FIG. 7 is a schematic view of a shade guide member in accordance with the invention.
Figure 8:
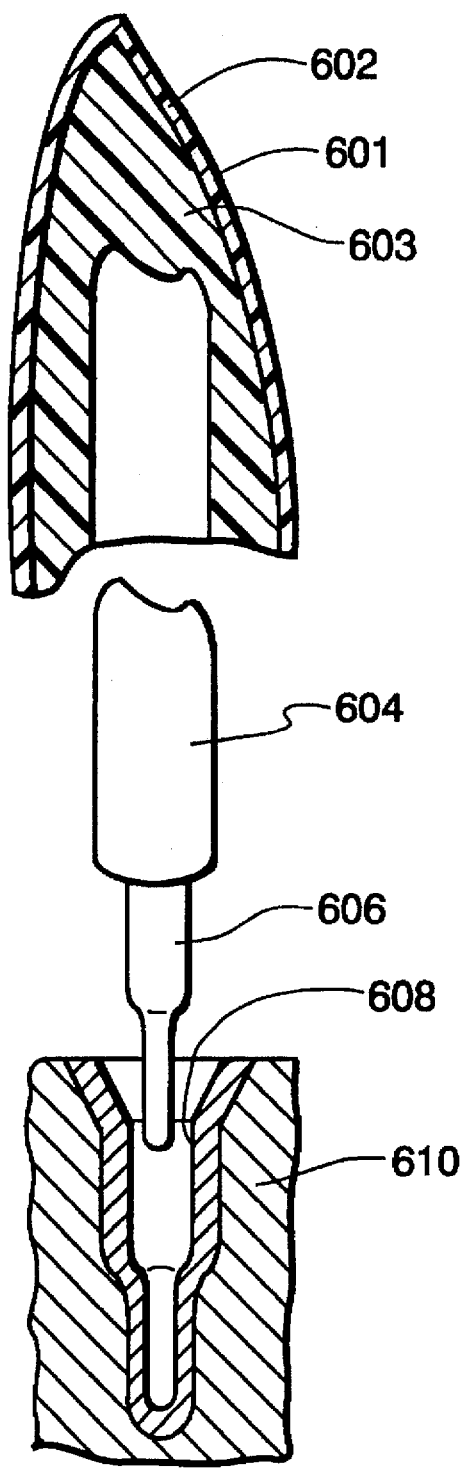
FIG. 8 is a schematic side cross sectional view of an implant crown in accordance with the invention.

Prosthetic teeth such as tooth 100 ae useful for making full and/or partial dentures, crowns, implant teeth and shade guide. FIG. 7 shows a shade guide arm 500 supporting prosthetic tooth 502. Arm 500 has bends 504 and 506. Tooth 502 is connected to arm 500 by connector 508. An implant crown 601 has an enamel layer 602 having a zone of substantially constant thickness and a shade layer 603 as shown in FIG. 8. Crown 601 is supported by core 604. Core 604 is connected to post 606. Post 606 is supported by sleeve 608. Sleeve 608 is bonded to carbon implant 610.

In accordance with a preferred embodiment of the invention digital information or data representative of a tooth enamel outer surface is prepared or retrieved from memory of a computer loaded with CAD/CAM software program, for example a Sabre 5000 CAD/CAM System, available from Gerber Systems Technology, Inc., South Windsor, Conn. The data is edited using the CAD/CAM system and two and/or three dimensional model(s) displayed on a video display monitor. The operator then offset a copy of enamel outer surface and edit the copy to design and shader outer surface. Once an acceptable surface pattern is generated.

Software is used to generate a tool path program for the making of the dental mold. The data in the form of the numerical coordinates of the tool path program are collected on a memory disk and down loaded or transferred to a floppy disk.

In accordance with a preferred embodiment of the invention the floppy disk is down loaded into the hard disk drive of a milling, driving, boring and contouring machine for example a BostoMatic Model 312-1S Vertical CNC Bed Type Precision Milling, Drilling, Boring and Contouring Machine, available from Boston Digital Corporation, Milford, Mass. The tool path program is used to direct and control the machine in the fabrication of the tooth mold. The feed rate average is 6 inches per minute (range 4.5–10 inches per minute), at 30,000 rpm, for four consecutive passes with mills of decreasing size. A quarter inch end mill (Bassett) is followed by an eighth inch end mill (Bassett), followed by a sixteenth inch ball end mill (Bassett), followed by a thirty-second inch ball end mill (TSC Carbide). The tool path accuracy is 0.0002 inch and the stepover range is 0.0005–0.001 inch. The machine has four axis capability but only three axes were used in the making of the mold. The mold is cut into a block of 416 free machining stainless steel. The resultant mold is tested for surface finish qualities by subjective visual evaluation with the trained eye at 7× magnification comparing stone impressions from the mold with the aluminum bronze master die. The machined mold contains approximately 95% of the surface detail and finish of the master die. The mold is a coupon that is mounted into a standard aluminum mold frame for proof molding.

Finish-polishing is accomplished with the finish tool path program for example using a finish-polishing tool. The finish-polishing tool comprises a hard wood polishing stick and is used with a diamond paste; the finish-polishing step is used to get as close as possible to the complete and acceptable surface detail and finish. A final hand polishing step may be carried out using a dental handpiece (power tool), brush (synthetic bristles), and jewelers' rouge.

For making the back mold part, the digitized information from the scan of the aluminum bronze master die is processed up to readiness to be down loaded into the hard disk drive of the milling machine. For making the shader mold part, a soft Babbitt master shader die (not coated with a glarefree substance) is placed on a revolving support and processed in the same manner as the aluminum bronze master die described above. The data is processed in the same manner as for the aluminum bronze master die information up to readiness to be down loaded into the hard disk drive of the milling machine. The data is smoothed on the screen during editing to assure the fit of the shader mold part into the face mold part.

In accordance with a preferred embodiment of the invention is provided a method of repeatedly molding high definition artificial dental teeth each having a molded enamel layer (coating). The method optionally includes scanning a model of a dental tooth. The method includes milling to make at least three mold parts. Each part is milled with a first mill by executing a first pass along a first tool path to remove material to form multiple cavities in a first metal block to make a multiple cavity mold part adapted to form multiple dental prosthetic teeth. The milling is directed by a milling program which uses edited data. The edited data is obtained by editing reflection data using a design program. The reflection data is representative of the surface of the tooth model. The edited data is representative of the surface of the dental artificial teeth. The edited data is adapted by the milling program to direct the milling along the tool path. The mold parts are used to repeatedly mold high definition artificial dental teeth each having a molded enamel layer (coating). When scanning of a model is used each said cavity is the negative of a portion of the model of a dental tooth to be molded in the mold. The program is produced by the steps of imaging the surface contours of the dental model and producing data readings in response to the imaging of the surface contours of the model.

In accordance with an embodiment of the invention is provided a method of making artificial dental teeth each having a molded enamel layer (coating) and high definition labial striations. Optionally a dental tooth model is provided scanned. Reflections from the tooth model are received, translated into electronic signals, which are then converted into reflection data. The reflection data is edited to add high definition labial striations using a design program to provide edited data and fabricating a metal tooth mold part. The fabricating step comprising using the edited data to direct machine milling of said tooth mold part. The milling comprising making a first pass with a first mill and making a second pass with a second mill, the first mill having a first mill end, the second mill having a second mill end, the second mill end being smaller in size than the first mill end, High definition artificial teeth are repeatedly molded using the mold part. Each tooth has a molded enamel layer (coating) and high definition labial striations. The scanning may comprise directing a laser beam onto the dental tooth model. The optional scanning step may include rotating the dental tooth model during said subjecting and receiving steps. The tooth model may be a three-dimensional wax or metal containing replica of a tooth.

The model may have a glare-free coating. The processing step may include creating an edited three-dimensional surface pattern of the tooth model from the edited data, evaluating the surface pattern of the dental tooth model, and creating a tool path program from the edited data. The evaluating step may include visual analysis of the surface pattern of the dental tooth model and comparison to known geometric values for the tooth model. The fabricating step may include using said tool path program to finish-polish the dental tooth mold part.

In accordance with a preferred embodiment of the invention is provided a method of molding artificial dental teeth each having a molded coating and labial striations. Optionally the method includes scanning a three-dimensional replica of a tooth having three-dimensional surface locations while rotating the replica. The reflections from said replica are received and translated into electronic signals, which are digitized into reflection data. The reflection data is edited to add high definition labial striations in a computer using a CAD/CAM program. A tool path program is created using the edited data. The tooth mold is fabricated using the tool path program to direct machine milling of a first, second and third metal artificial dental teeth mold parts. The milling of the first metal mold part from a first metal part includes making a first pass with a first mill and making a second pass with a second mill to mill the first metal part. The first mill has a first mill end. The second mill has a second mill end. The second mill end is smaller in size than said first mill end.

The milling of the second metal mold part from a second metal part including making a first pass with the first mill and making a second pass with the second mill to mill the second mold part.

The milling of the third metal mold part from a third metal part includes making a first pass with the first mill and making a second pass with the second mill to mill the third mold part.

The fabricating step may use the tool path program to direct machine finishing-polishing the mold part. Preferably polishing of at least one of the mold parts is directed by a finish tool path program. Preferably milling a pattern of a layer of dental prosthetic tooth to make a mold is directed by a milling program which uses edited data. The edited data is preferably provided by editing reflection data using a design program. The reflection data is representative of the surface of a tooth model. The edited data being representative of the surface of said edited dental prosthetic tooth. The data is adapted by the milling program to direct the milling.

The polishing preferably includes finish-polishing using a finish tool path and a finish-polish tool, such as a wood tool. The tool is preferably used with a paste, such as diamond paste.

In accordance with a preferred embodiment of the invention is provided a method of molding artificial dental teeth each having a molded enamel layer (coating) and labial striations. The method includes milling multiple patterns of layers of artificial teeth in first and second portions of mold making material to make first and second mold parts. The milling is directed by a milling program which uses edited data. The edited data is provided by editing reflection data using a design program. The reflection data is representative of the surface of a tooth model. The edited data is representative of the surface of the artificial tooth. The edited data is adapted by the milling program to direct the milling of said first and second mold parts. The milling of the first mold part includes executing a first pass with a first mill and executing a second pass with a second mill. The first mill has a first mill end. The second mill has a second mill end. The second mill end is smaller in size than the first mill end. The milling of the second mold part includes executing a first pass with a third mill and executing a second pass with a fourth mill. The third mill has a third mill end. The fourth mill has a fourth mill end. The third mill end is smaller in size than the fourth mill end. By repeatedly molding polymerizable material in the mold high definition artificial dental teeth are formed each having a molded polymerizable material enamel layer (coating) and labial striations.

Preferably the mold making material is readily machinable and polishable, such as steel, nickel, aluminum, ceramic or plastic.

Preferably the mold making material is steel, nickel, aluminum, ceramic or plastic. Preferably the milling includes making a second pass along the tool path with a second mill having a second mill end. The second mill end is smaller in size than the first mill end. Preferably the milling includes a making third pass along the tool path with a third mill having a third mill end. The third mill end is smaller in size than the second mill end. Preferably the milling includes making a fourth pass with a fourth mill having a fourth mill end. The fourth mill end is smaller in size than the third mill end. Preferably the mold part is a face mold part, a shader mold part, a second back mold part or a back mold part. Preferably a point of contact with a second part is provided using a surface pattern of the mold. Preferably the milling with the first mill is by executing a first pass along a second tool path to remove material to form multiple cavities in a second block to make a multiple cavity second mold part. Preferably the milling with a second mill is by making a second pass along the second tool path to remove material from the second block.

It will be apparent to those skilled in the art that various modifications and changes may be made in the practice and use of the present invention without departing from the scope thereof as set forth in the following claims.

What is claimed is:

1. A family of prosthetic teeth comprising a first tooth in a first set of teeth having a first ratio of the shade layer length (S) to back length (B) and a second tooth in a second set of teeth having a second ratio of the shade layer length to back length, said first and second ratios being substantially equal.

2. The family of claim 1 wherein said end of first and second tooth is an incisor and said first ratio is within 5 percent of being equal to said second ratio.

3. A family of prosthetic teeth, comprising:
   a first tooth in a first set of teeth, said first tooth having
   a first overall labial length (L),
   and a first back length (B), and
   a second tooth in a second set of teeth, said second tooth having
   a second overall labial length, and
   a second back length,
   the ratio of the first overall labial length to the second overall labial length being substantially equal to the ratio of the first back length to the second back length.

4. The family of prosthetic teeth of claim 3 wherein said first tooth has a first shader length and said second tooth has a second length and the ratio of said first shader length to said first overall labial length is substantially equal to the ratio of said second shader length to said second overall labial length.

5. The family of teeth of claim 4 wherein each said tooth is a molar.

6. The family of teeth of claim 4 wherein each said tooth is an incisor.

7. The family of teeth of claim 4 wherein each said tooth is a canine.

8. The family of teeth of claim 4 wherein said first shader length is substantially equal to 68 percent of said first overall labial length.

9. The family of teeth of claim 3 wherein the ratio of the first overall labial length to the second overall labial length is within 5 percent of being equal to the ratio of the first back length to the second back length.

10. The family of teeth of claim 3 wherein each said tooth is an incisor.

11. The family of teeth of claim 3 wherein each said tooth is a canine.

12. The family of teeth of claim 3 wherein said first back length is substantially equal to 94 percent of said first overall labial length.

13. The family of teeth of claim 12 wherein said shader length is substantially equal to 68 percent of said overall labial length.

14. A family of prosthetic teeth, comprising:
   a first tooth in a first set of teeth, said first tooth having
   a first enamel layer,
   a first shade layer length, and
   a first back length, and
   a second tooth in a second set of teeth, said second tooth having
   a second enamel layer,
   a second shade layer length, and
   a second back length,
   the ratio of the first shade layer length to the second shade layer length being substantially equal to the ratio of the first back length to the second back length.

15. The set of prosthetic teeth of claim 14 wherein said first tooth has a first overall labial length and said second tooth has a second overall labial length and the ratio of said first shade layer length to said first overall labial length is substantially equal to the ratio of said second shade layer length to said second overall labial length.

16. The set of teeth of claim 15 wherein each said tooth is a molar.

17. The set of teeth of claim 15 wherein each said tooth is an incisor.

18. The set of teeth of claim 15 wherein each said tooth is a canine.

19. The set of teeth of claim 15 wherein said first shader length is substantially equal to 68 percent of said first overall labial length.

20. The set of teeth of claim 14 wherein the ratio of the first shade layer length to the second shade layer length is within 5 percent of being equal to the ratio of the first back length to the second back length.

21. The set of teeth of claim 14 wherein each said tooth is an incisor.

22. The set of teeth of claim 14 wherein each said tooth is a canine.

23. The set of teeth of claim 14 wherein said first back length is substantially equal to 94 percent of said first overall labial length.

24. The set of teeth of claim 23 wherein said shader length is substantially equal to 68 percent of said overall labial length.

* * * * *